US007942827B2

(12) United States Patent
Mir et al.

(10) Patent No.: US 7,942,827 B2
(45) Date of Patent: May 17, 2011

(54) MINIMALLY INVASIVE ALLERGY TESTING SYSTEM

(75) Inventors: Jose Mir, Rochester, NY (US); Dennis Roland Zander, Penfield, NY (US)

(73) Assignee: Infotonics Technology Center, Inc., Canandaigua, NY (US)

(*) Notice: Subject to any disclaimer, the term of this patent is extended or adjusted under 35 U.S.C. 154(b) by 35 days.

(21) Appl. No.: 11/995,366

(22) PCT Filed: Jul. 11, 2006

(86) PCT No.: PCT/US2006/026774
§ 371 (c)(1),
(2), (4) Date: Jan. 11, 2008

(87) PCT Pub. No.: WO2007/008824
PCT Pub. Date: Jan. 18, 2007

(65) Prior Publication Data
US 2008/0269635 A1   Oct. 30, 2008

Related U.S. Application Data

(60) Provisional application No. 60/698,202, filed on Jul. 11, 2005.

(51) Int. Cl.
*A61B 5/00* (2006.01)
(52) U.S. Cl. ........................................ 600/556
(58) Field of Classification Search ............ 600/566
See application file for complete search history.

(56) References Cited

U.S. PATENT DOCUMENTS 4,862,894 A * 9/1989 Fujii .......................... 600/479
(Continued)

FOREIGN PATENT DOCUMENTS

EP          1086718          3/2001

OTHER PUBLICATIONS

Schuster et al. "Macro-Video documentation patch tests," Contact Dermatitis 2005: 52: 177-183 (Apr. 27, 2005).*

(Continued)

*Primary Examiner* — Max Hindenburg
*Assistant Examiner* — Michael C Stout
(74) *Attorney, Agent, or Firm* — LeClairRyan

(57) ABSTRACT

An allergy testing system includes encapsulated allergens, a microneedle array, and an activation system coupled to the microneedle array and the encapsulated allergens such that the encapsulated allergens are moved into contact with a subject as the microneedle array is moved from a resting position to a penetrating position. A method for determining a degree of reaction to one or more allergens by a patient in a minimally invasive manner is also disclosed. Penetration of one or more microneedles into a skin of the patient is caused. Each of the penetrations into the skin is exposed with an allergen from each of the one or more microneedles. One or more images are captured of each of the penetrations into the skin. Each of the captured images are analyzed to assess the degree of reaction to the specific allergen. Allergic reactivity data is output for at least one of the allergens.

31 Claims, 17 Drawing Sheets

U.S. PATENT DOCUMENTS

| | | | |
|---|---|---|---|
| 5,054,896 A * | 10/1991 | Margolis | 359/379 |
| 5,097,810 A * | 3/1992 | Fishman et al. | 600/556 |
| 5,099,857 A * | 3/1992 | Baldo et al. | 600/556 |
| 5,457,041 A | 10/1995 | Ginaven et al. | |
| 6,024,925 A * | 2/2000 | Little et al. | 422/100 |
| 6,355,054 B1 * | 3/2002 | Neuberger | 607/89 |
| 6,692,456 B1 | 2/2004 | Eppstein et al. | |
| 6,934,438 B2 * | 8/2005 | Hoke | 385/16 |
| 2003/0218756 A1 * | 11/2003 | Chen et al. | 356/497 |
| 2004/0176701 A1 * | 9/2004 | Fujii | 600/556 |
| 2005/0171480 A1 * | 8/2005 | Mukerjee et al. | 604/173 |
| 2005/0228313 A1 * | 10/2005 | Kaler et al. | 600/583 |

OTHER PUBLICATIONS

Cula et al. (Bidirectional Imaging and Modeling of Skin Texture, Proceedings of Texture 2003, Oct. 17, 2003, Nice, France.*

DFW-V500, Technical Manual.*

Dave Litwiller CCD vs CMOS: Facts and Fiction, Jan. 2001 Photonics Spectra.*

Proximity Series: InfiniMini.*

* cited by examiner

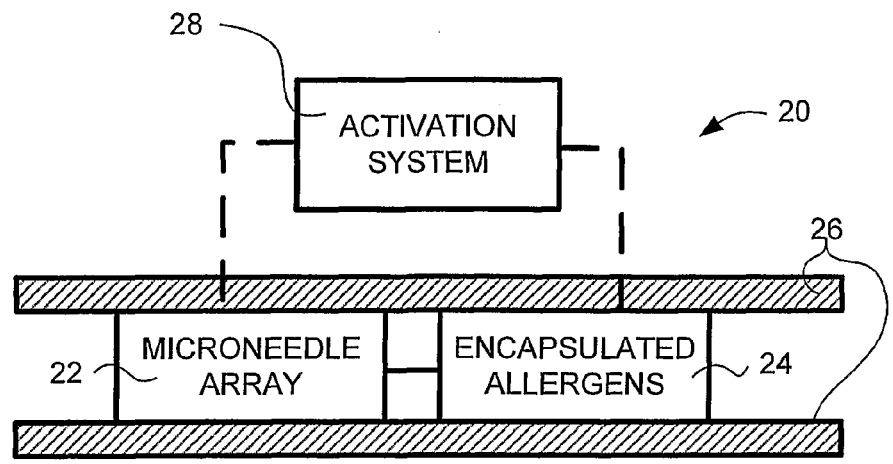
FIG. 1
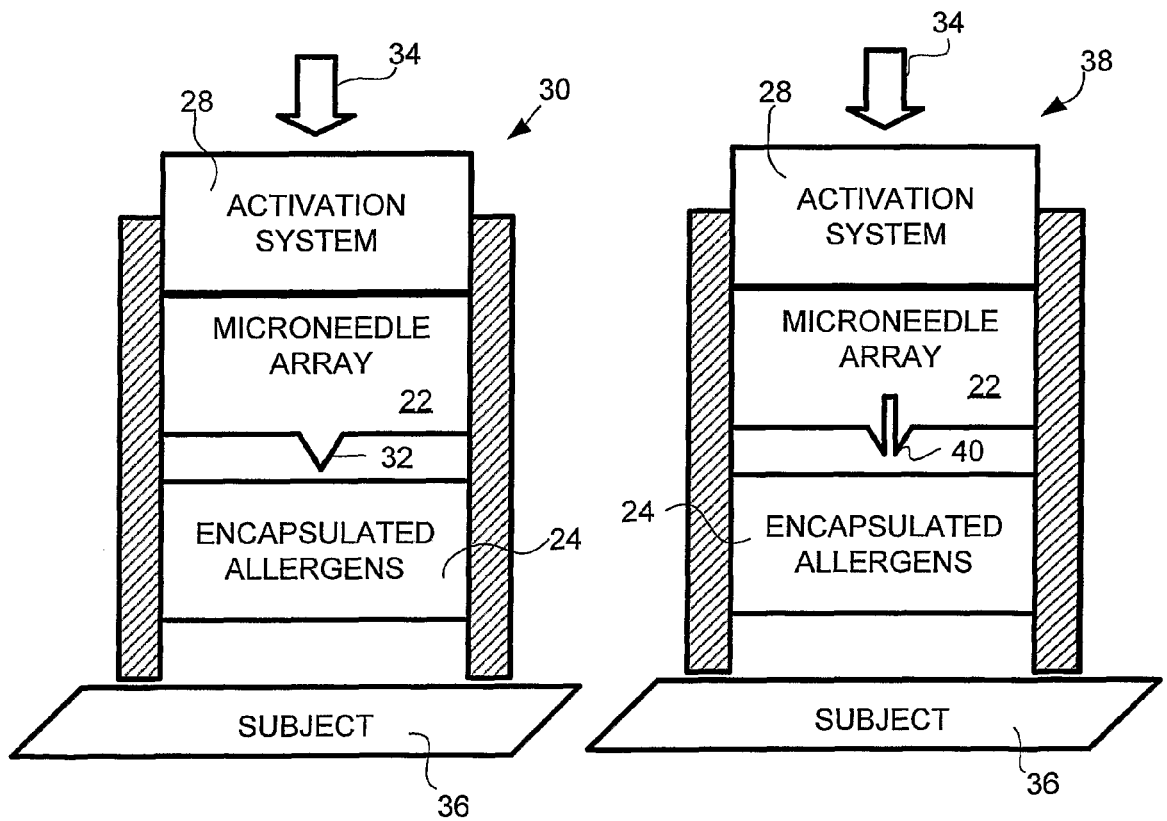
FIG. 2A
FIG. 2B

MINIMALLY INVASIVE ALLERGY TESTING SYSTEM

RELATED APPLICATIONS

This application claims priority to U.S. provisional patent application No. 60/698,202 filed Jul. 11, 2005, the specification of which is hereby officially incorporated by reference in its entirety,

FIELD

The claimed invention generally relates to systems and methods for testing for medical conditions and, more particularly, to systems used to determine a degree of reaction to one or more allergens by a subject in a minimally invasive manner.

BACKGROUND

It is estimated that at least 50% of the population has some form of allergy. Approximately 20 million patients are currently tested for allergies using a number of techniques, for example, skin prick test, intradermal test, blood test, and skin patch test. Allergy test methods, such as the skin prick test are invasive and manual, involving depositing drops of many allergens on a subject's back, forearm, or other smooth body surface, labeling the region for identification, and then pricking the region with a needle to allow penetration of the allergy into the subject's body. The intradermal test is even more invasive, involving injecting a small amount of various allergens into the subject's skin. Due to the nature of these processes, large areas of the subject's skin tend to be affected.

Subjects undergoing these pin prick and intradermal tests then wait a prescribed period of time to allow the allergens a chance to react with their skin. Test regions must be large enough to easily be identified and evaluated by the human eye or by photographs which are then printed or enlarged. Although these forms of allergy testing often cover a large area of a patient's body, these manual determinations of allergic reaction provide the medical practitioner with a snapshot in time which has been shown to be useful in screening patients for allergic reactions.

Blood testing provides a highly invasive, yet possibly more convenient method of allergy testing. Unfortunately, blood testing does not surpass the sensitivity, specificity, and predictive value of the skin test. Blood test results are often dependent upon the laboratory which is performing the test. Blood testing for allergies is also a more expensive option.

Therefore, there is a need for a minimally invasive allergy testing system which does not need to cover large areas of a patient's skin, which can be automated to a large extent, which can be correlated to existing skin testing data, which offers more than a snapshot in time of an allergic reaction, which is economical, and which is easy to use and manufacture.

SUMMARY

An allergy testing system is disclosed. The allergy testing system includes encapsulated allergens, a microneedle array, and an activation system coupled to the microneedle array and the encapsulated allergens such that the encapsulated allergens are moved into contact with a subject as the microneedle array is moved from a resting position to a penetrating position.

An imaging system for use with a minimally invasive allergy testing system is disclosed. The imaging system includes an image sensor, an alignment guide to align the image sensor with an allergy test area, and an optics system configured to couple an image of the allergy test area to the image sensor. The imaging system also includes an analyzer coupled to the image sensor.

Another allergy testing system is disclosed. The allergy testing system includes an attachment band having a test frame, wherein the test frame defines an opening in the attachment band. The allergy testing system also includes a package, for interfacing with the test frame, comprising a microneedle array and encapsulated allergens. The allergy testing system further includes an imaging system for interfacing with the test frame. The allergy testing system also includes an analyzer coupled to the imaging system.

A method for determining a degree of reaction to one or more allergens by a patient in a minimally invasive manner is disclosed. Penetration of one or more microneedles into a skin of the patient is caused. Each of the penetrations into the skin is exposed with an allergen from each of the one or more microneedles. One or more images are captured of each of the penetrations into the skin. Each of the captured images are analyzed to assess the degree of reaction to the specific allergen. Allergic reactivity data is output for at least one of the allergens.

The claimed invention provides a system and method to minimize the invasiveness of allergy testing, degree and area of reaction, testing time, general discomfort, and risk of infection. Another advantage of the claimed invention is that it enables a much smaller test area footprint when compared to prior testing devices. The much smaller footprint also simplifies and expedites the allergy testing process for a medical staff. The claimed invention is compatible with micro-fluidic technology, and therefore much smaller quantities of allergens may be dispensed, reducing the severity of the reaction for a patient, and possibly reducing the cost for the testing. The allergen dispensing process may also be automated in some embodiments, allowing for automated and quantified allergy reactivity data readout, thereby reducing uncertainty and subjectivity. A further advantage possible with automated embodiments is the ability to capture continuous or nearly continuous visual images of an allergy test site. This allows scientist and medical personnel the chance to study the time rate of change for certain allergic reactions, and better understand a patient's reaction and sensitivity. Overall, the minimally invasive allergy testing system enables a relatively fast allergy test cycle time, lowers the cost of such testing, and significantly reduces the chance for errors.

BRIEF DESCRIPTION OF THE DRAWINGS

FIGS. 1-2E schematically illustrate embodiments of an allergy testing system.

FIGS. 3A & 3B to FIGS. 8A & 8B schematically illustrate side views (A) and top views (B), respectively, of embodiments of microneedles for use in an allergy testing system.

FIGS. 12D1-12D4 schematically illustrate different embodiments of gathering and analyzing allergy test data after the allergens have been applied by the allergy testing system in FIGS. 12A-12C.

DETAILED DESCRIPTION

Figure 12A:
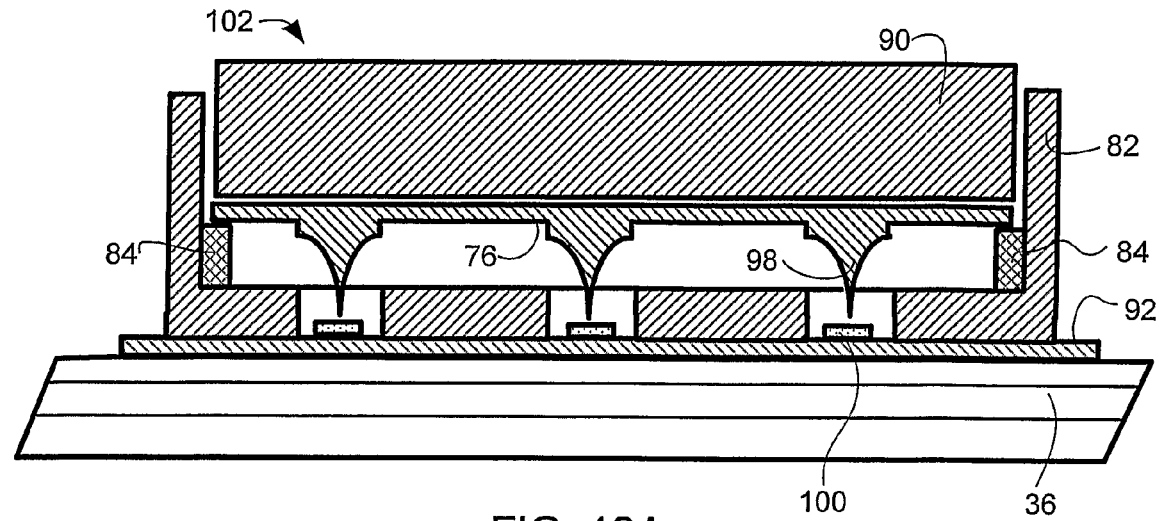
FIGS. 12A-12C schematically illustrate one possible method of applying allergens to a subject using an embodiment of an allergy testing system.
Figure 12B:
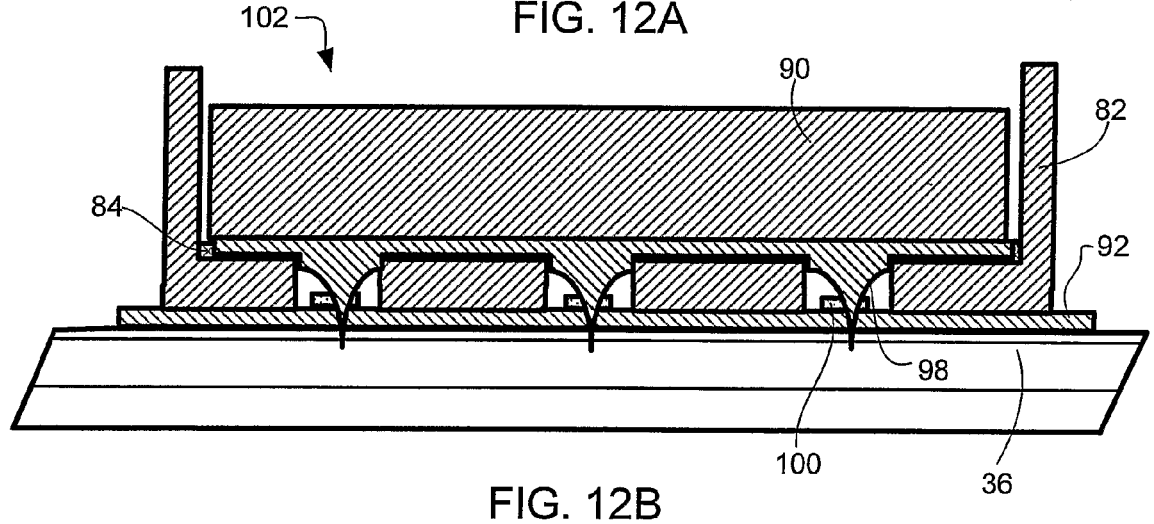
Figure 12C:
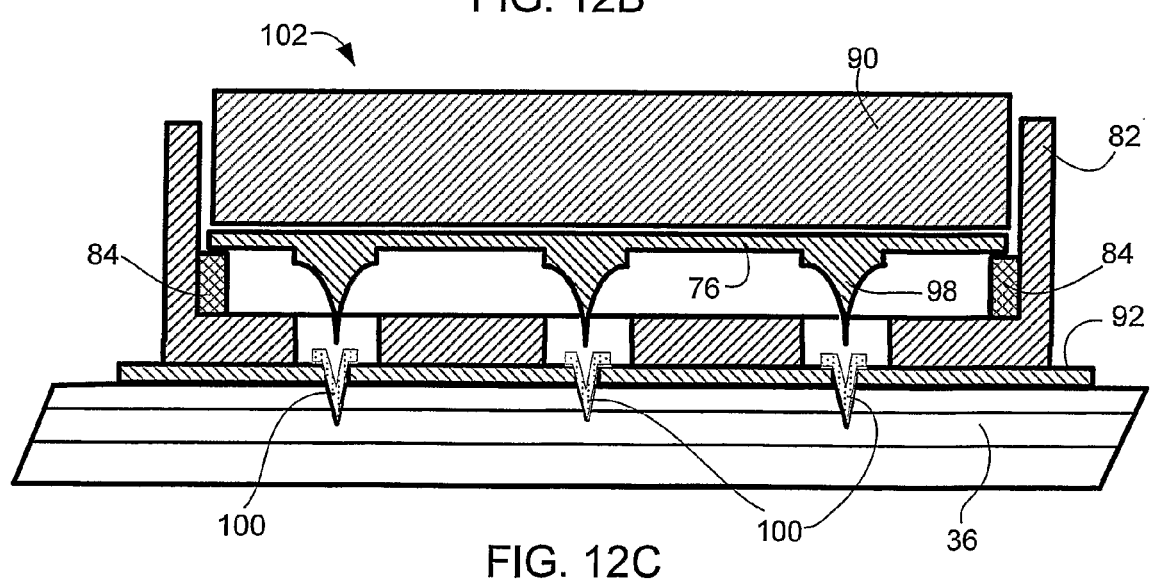
Figures 1, 12D:
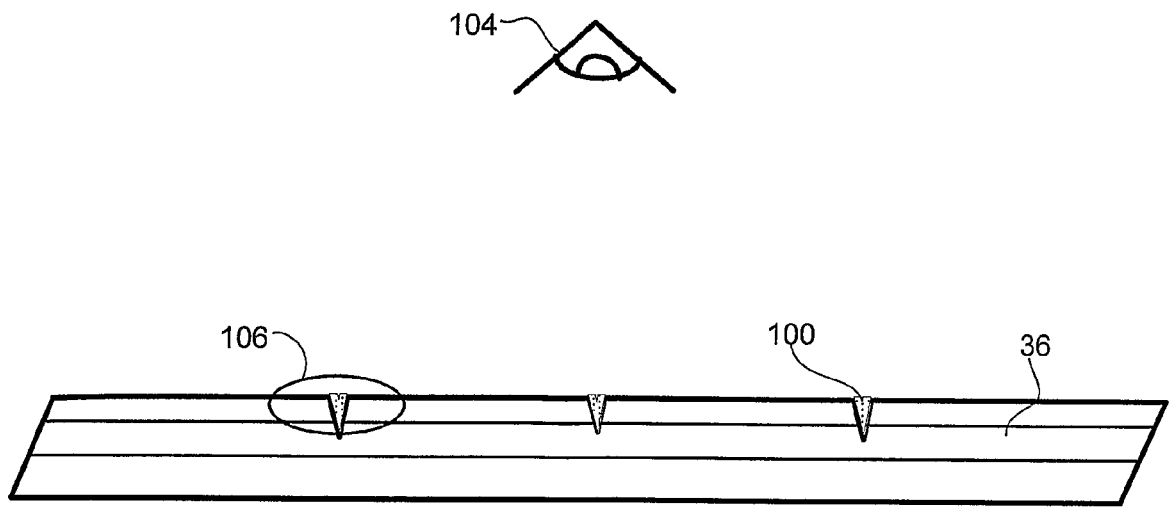

FIG. 1 schematically illustrates an embodiment of a minimally invasive allergy testing system 20. The minimally invasive allergy testing system 20 has a microneedle array 22 which is coupled to an array of encapsulated allergens 24. The microneedle array 22 has at least one microneedle, and preferably a plurality of microneedles which may be spaced in a linear array, a two-dimensional array, or any other spacing desired. The microneedles 22 may have a height of about 50-300 microns and a diameter of about 10-80 microns in order to penetrate a subject's skin, although other embodiments may have other dimensions. (Skin not illustrated in this view.) The microneedle array may be manufactured out of a number of different substances, for example, silicon, glass, metal, quartz, or plastic. Due to its attractive micromachining properties, silicon may be anisotropically etched using chemical and reactive ion etching processes to fabricate the microneedles, although other materials and manufacturing processes can be used.

The encapsulated allergens 24 have a corresponding set of allergens associated with the microneedles in the microneedle array 22. The microneedle array 22 and the encapsulated allergens 24 may be held in alignment with each other by a package 26. The minimally invasive allergy testing system 20 also has an activation system 28 which may be directly or indirectly coupled to the microneedle array 22 and/or the encapsulated allergens 24. The activation system 28 causes a skin of a test subject to be pricked, while releasing corresponding encapsulated allergens 24 into contact with the appropriate test prick.

There is a great degree of flexibility in configuring the activation system 28. In some embodiments, the activation system 28 can be a mechanical plunger or other mechanical system, which is pressed by a medical professional, or even the test subject themselves. In other embodiments, the activation system 28 can be a spring-loaded release which allows a predictable force to be applied to the microneedle array 22 as it pricks the subject's skin. Further embodiments of an allergy testing system 20 may have an activation system which is an electro-mechanical system, such as a solenoid, motor, or a micromechanical actuator.

The microneedle array 22, the encapsulated allergens 24, and/or the activation system 28 may be separate components of the allergy testing system 20. In the embodiment illustrated in FIG. 1, the microneedle array 22 and the encapsulated allergens 24 are removeably packaged from the activation system 28. This removability allows for designs and embodiments with simple replacement of the microneedles and encapsulated allergens which are typically only used once.

Figures 2C, 2D, 2E:
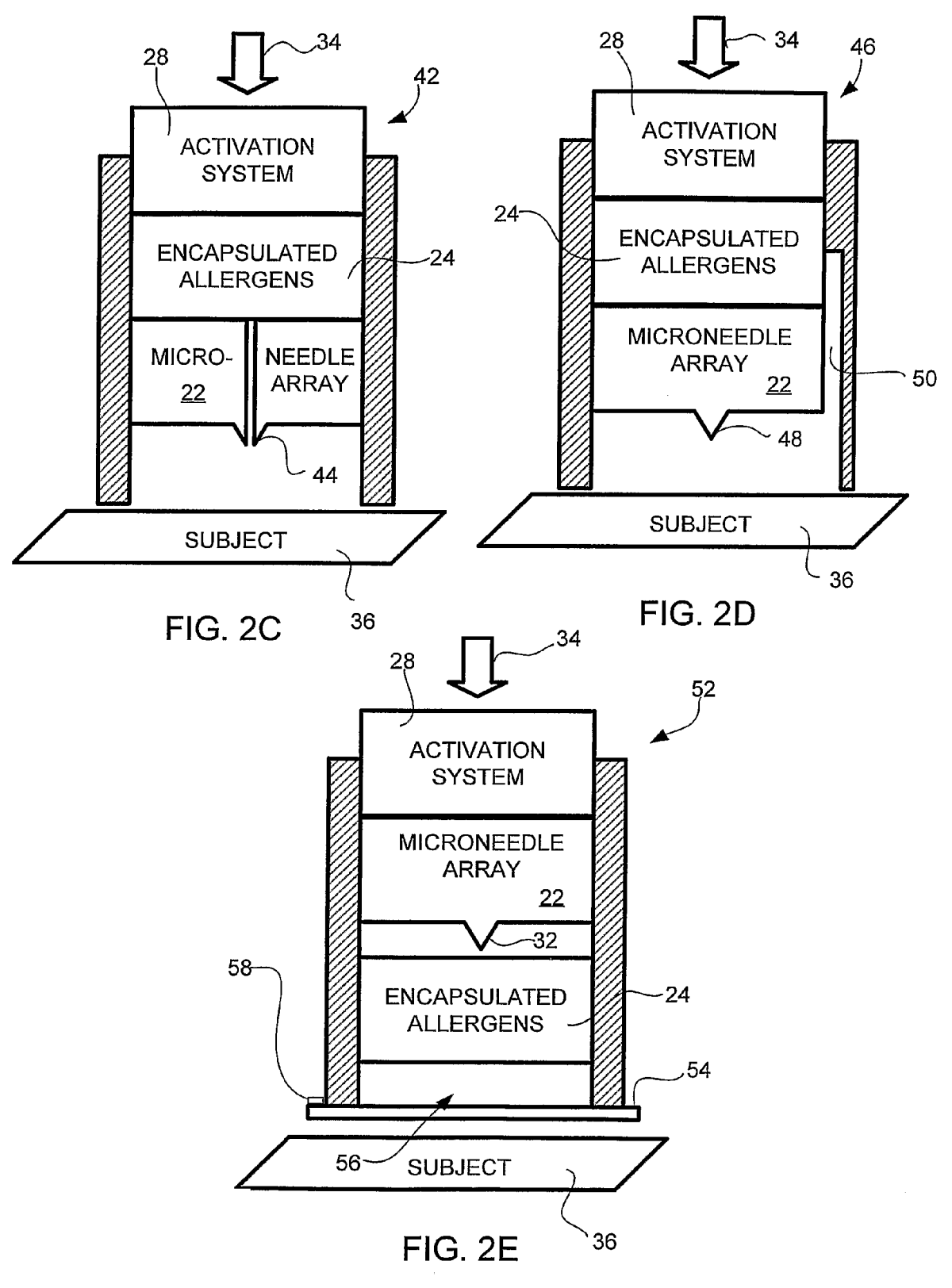
Figures 2, 12D:
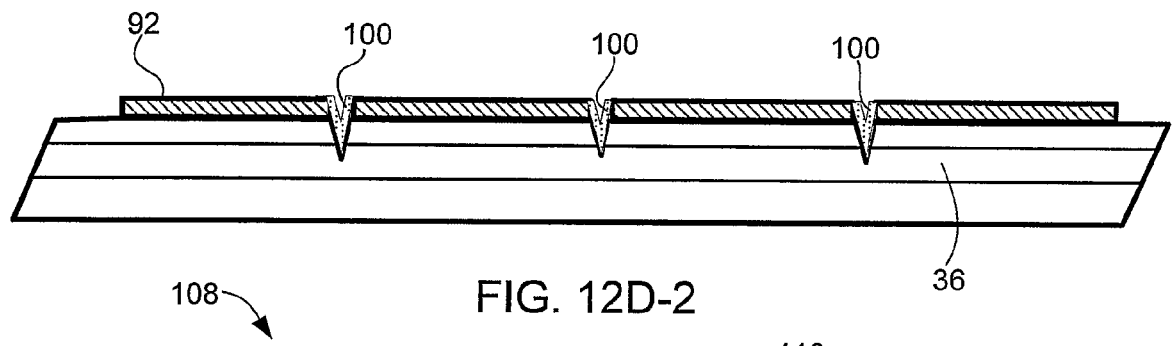

FIG. 2A illustrates another embodiment of an allergy testing system 30. This allergy testing system 30 has the microneedle array 22 directly coupled to the activation system 28. The microneedle array 22 may still be removeably coupled to the activation system 28 in some embodiments. For simplicity, the microneedle array 22 is schematically illustrated in this and other embodiments as only having a single needle 32. It should be understood that any number of microneedles 32 may be present on the microneedle array 22, depending on size of the microneedle array 22 and the number of allergy test sites desired. The needles 32 of the microneedle array 22 are positioned to contact the encapsulated allergens 24 as the activation system 28 is engaged. In the orientation of FIG. 2A, the activation system 28 will engage downwards 34 to push the microneedles 32 of the microneedle array 22 through the corresponding encapsulated allergen sites, and then on into a subject's skin 36. In this embodiment, the microneedles 32 are wetted with the allergens before the skin 36 is pierced.

FIG. 2B schematically illustrates an allergy testing system 38 which is similar to the allergy testing system of FIG. 2A, with the addition of at least one hollow microneedle 40 in the microneedle array 22. In this embodiment, when the hollow microneedle 40 pierces the encapsulated allergens 24, the allergens may be drawn into the hollow portion of the microneedle 40, which may then deposit the allergens deeper within the subject's skin 36 after the microneedle pierces the skin 36. The allergens will also coat the outside of the microneedle 40, similar to the embodiment of FIG. 2A.

FIG. 2C schematically illustrates another embodiment of a minimally invasive allergy testing system 42. This allergy testing system 42 has the microneedle array 22 indirectly coupled to the activation system 28. The microneedle array 22 may still be removeably coupled to the activation system 28 in some embodiments. The needles 44 of the microneedle array 22 are hollowed-through and the side of the microneedle array 22 opposite the hollowed microneedle 44 is arranged to contact the encapsulated allergens 24 when the activation system 28 is engaged. In the orientation of FIG. 2C, the activation system 28 will engage downwards 34 to push encapsulated allergens 24 through the corresponding hollowed microneedle 44, and then on into a subject's skin 36.

FIG. 2D schematically illustrates another embodiment of a minimally invasive allergy testing system 46. Similar to the embodiment of FIG. 2C, this allergy testing system 46 has the microneedle array 22 indirectly coupled to the activation system 28. The microneedle array 22 may still be removeably coupled to the activation system 28 in some embodiments. The microneedles 48 in this embodiment are not hollow microneedles. Instead, when the activation system 28 is engaged (downwards in the orientation of FIG. 2D), the activation system 28 will squeeze the encapsulated allergens 24 through a groove or channel 50 near the microneedle array 22. The activation system 28 indirectly pushes the microneedle array 22 into contact with the subject 36 before, after, or while the allergens arrive at the prick location. The timing of the arrival of the allergens may be controlled by several parameters, including, for example, changing the viscosity of the allergens, building in a desired flow resistance in the allergen channel 50, and/or, choosing the strength of the allergen encapsulation to allow for a quick or a slow release of the allergens.

FIG. 2E is a further embodiment of an allergy testing system 52. This embodiment is similar in design and operation to the embodiment of FIG. 2A, with the addition of a sheet 54 to cover the orifice 56 where the allergen will be applied by the microneedle 32. The sheet 54 may be a thin sealing film employed over at least a portion of the orifices and a surface of the package 26 to serve as a sterile layer between the subject's skin 36 and the encapsulated allergens 24 and/or the microneedle array 22. The sealing film 54 may be removed before use or left behind on the patient's skin 36. If left behind on the patient's skin, the sealing film 54 may have a human readable code or a machine readable code, such as a barcode, or other identification marks 58. These identifying marks can be used for orientation in the analysis stage to be discussed later in this specification. The identifying marks can also identify the various allergens being used in one or more locations. The identifying marks may be pre-imaged on the sealing film 54, or they may be marked onto the film 54 with a microneedle 32 when the allergy test is performed. In some embodiments, the sealing film 54 may be transparent for ease in seeing the allergy test sites.

Figure 3A:
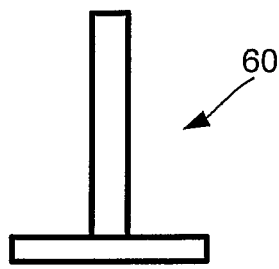
Figure 3B:
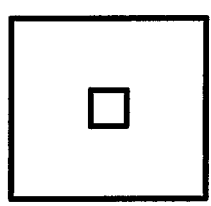

The microneedles in the microneedle array 22 may have a variety of geometries. FIGS. 3A and 3B schematically illustrate an embodiment of a microneedle 60 with a substantially square or rectangular cross-section in a side view and a corresponding top view, respectively.

Figure 4A:
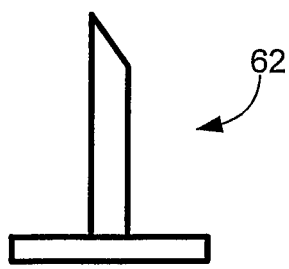
Figure 4B:
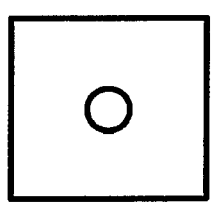

FIGS. 4A and 4B schematically illustrate an embodiment of a microneedle 62 with a substantially circular cross-section in a side view and a corresponding top view, respectively. The microneedle embodiment shown in FIG. 4A illustrates another variation possible with microneedle design. The microneedle 62 has a wedged top. Although other embodiments are not shown wedged, they could be modified in further embodiments to have a wedge-shaped top.

Figure 5A:
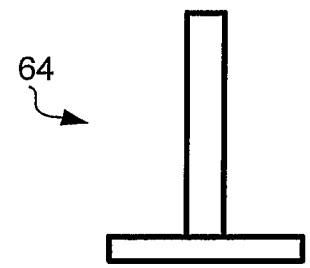
Figure 5B:
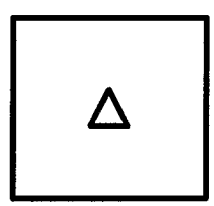

FIGS. 5A and 5B schematically illustrate an embodiment of a microneedle 64 with a substantially triangular cross-section in a side view and a corresponding top view, respectively.

Figure 6A:
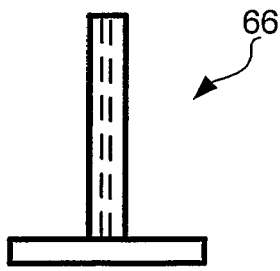
Figure 6B:
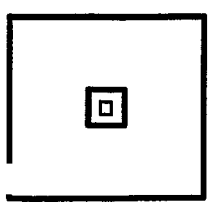

FIGS. 6A and 6B schematically illustrate an embodiment of a microneedle 66 with a substantially square or rectangular cross-section in a side view and a corresponding top view, respectively. This microneedle, however, is a hollow microneedle, having a channel formed within the needle for the passage of allergens.

Figure 7A:
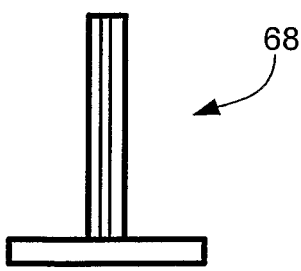
Figure 7B:
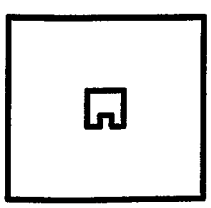

FIGS. 7A and 7B schematically illustrate an embodiment of a microneedle 68 with a substantially square or rectangular cross-section in a side view and a corresponding top view, respectively. This microneedle, however, is a grooved microneedle, having a channel formed on the side of the needle for the passage of allergens.

Figure 8A:
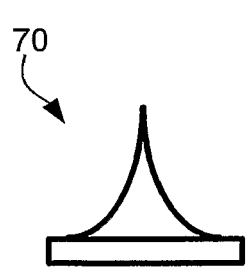
Figure 8B:
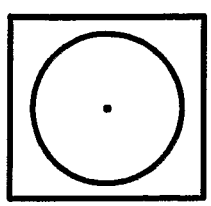

FIGS. 8A and 8B schematically illustrate an embodiment of a microneedle 70 with a changing cross-sectional area that tapers to a point.

Any of the features of the microneedles in the embodiments of FIGS. 3A-8B may be combined with one another, and cross-sectional shapes may be varied. For example, a microneedle could be both hollowed and grooved at the same time. As mentioned before, the microneedles may have a height of about 50-300 microns and a diameter of about 10-80 microns in order to penetrate a subject's skin, although other embodiments may have other dimensions. (Skin not illustrated in this view.) The microneedle array may be manufactured out of a number of different substances, for example, silicon, glass, metal, or plastic. Due to its attractive micromachining properties, silicon may be anisotropically etched using chemical and reactive ion etching processes to fabricate the microneedles, although other materials and manufacturing processes can be used.

Figure 9:
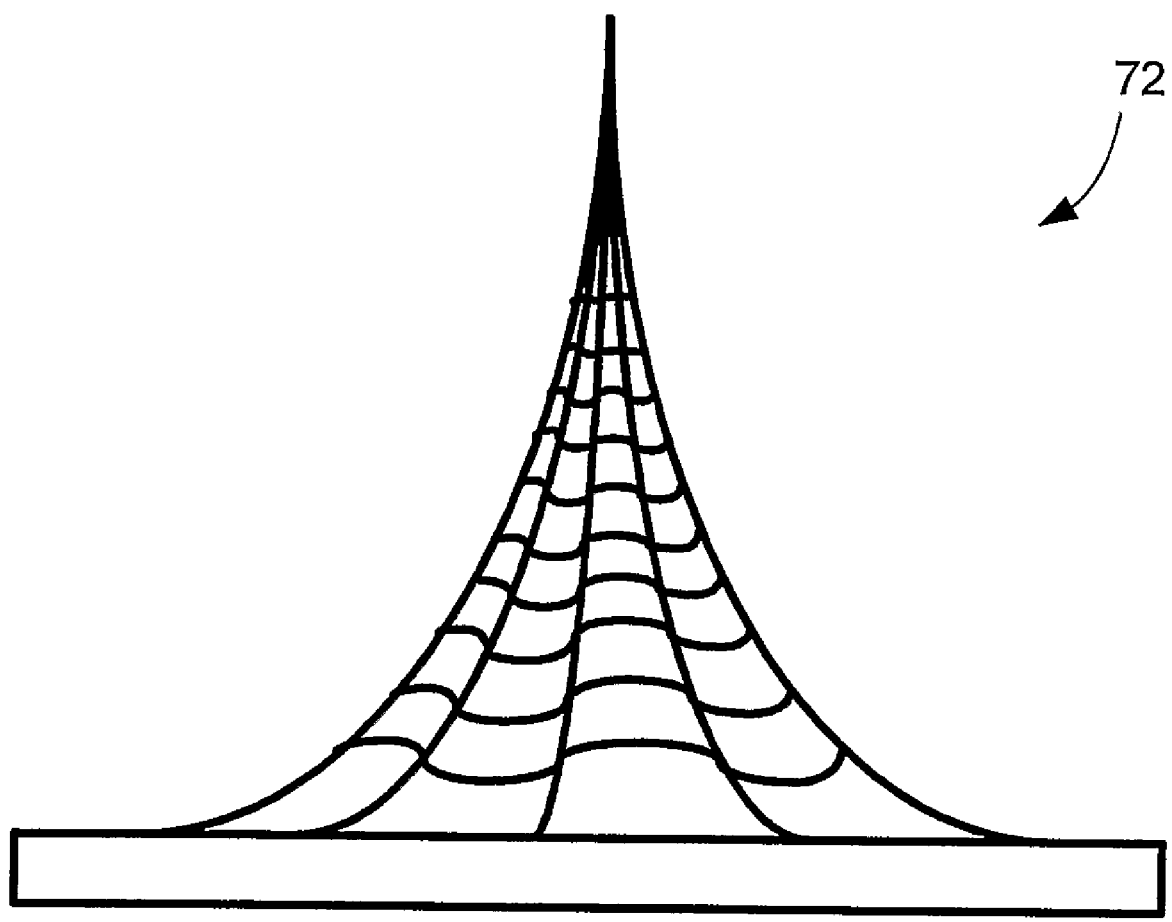
FIG. 9 schematically illustrates a side view of a corrugated microneedle embodiment for use in an allergy testing system.

A further embodiment of a microneedle 72 is schematically illustrated in FIG. 9. In this embodiment, the microneedle is corrugated around a generally pointed microneedle structure. Corrugated needle designs like this one may facilitate the entry and exit of the microneedle from the test subject 36 with a reduced amount of force. The corrugations may also provide channels for the allergens to enter a puncture site.

Figure 10A:
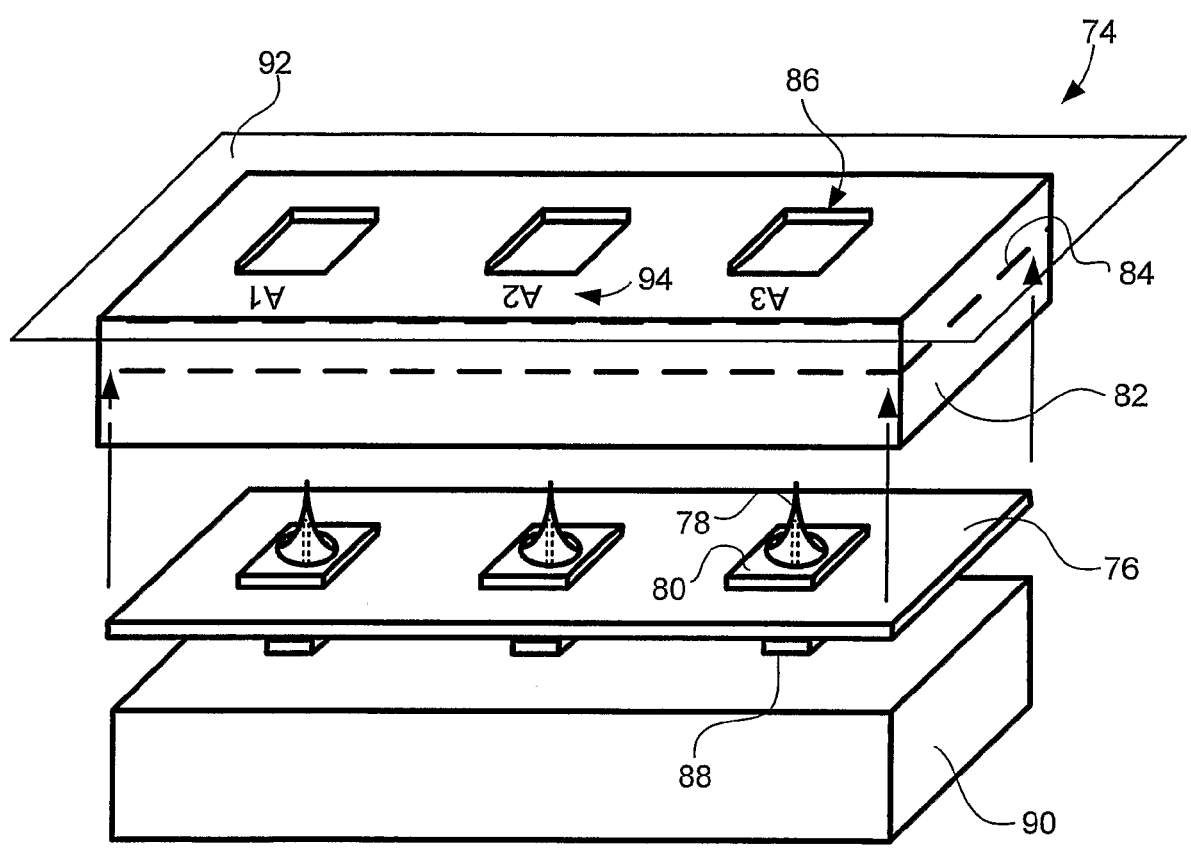
FIG. 10A schematically illustrates an exploded perspective view of an embodiment of an allergy testing system.
Figure 10B:
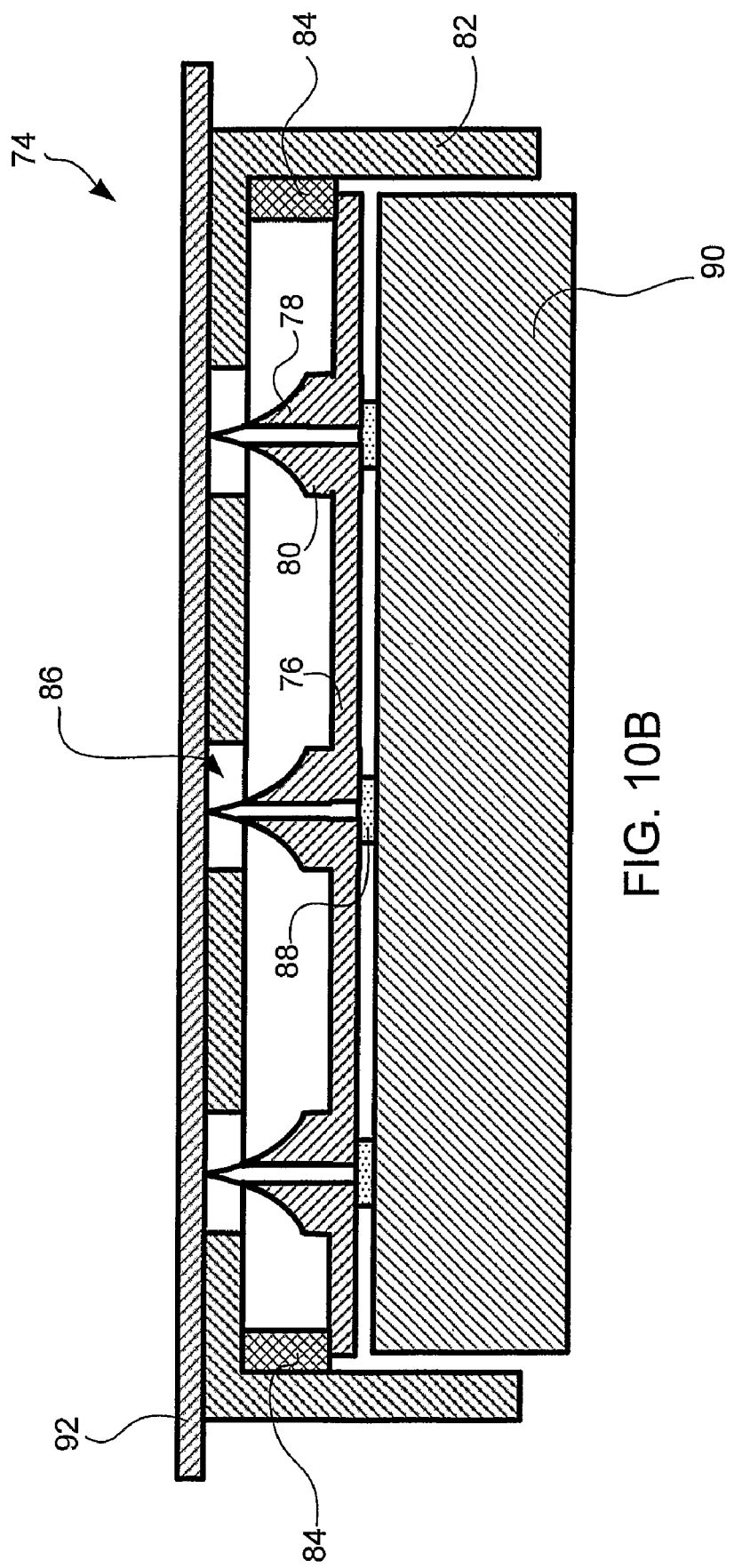
FIG. 10B schematically illustrates an assembled, cross-sectional view of the allergy testing system embodiment of FIG. 10A.
Figure 11A:
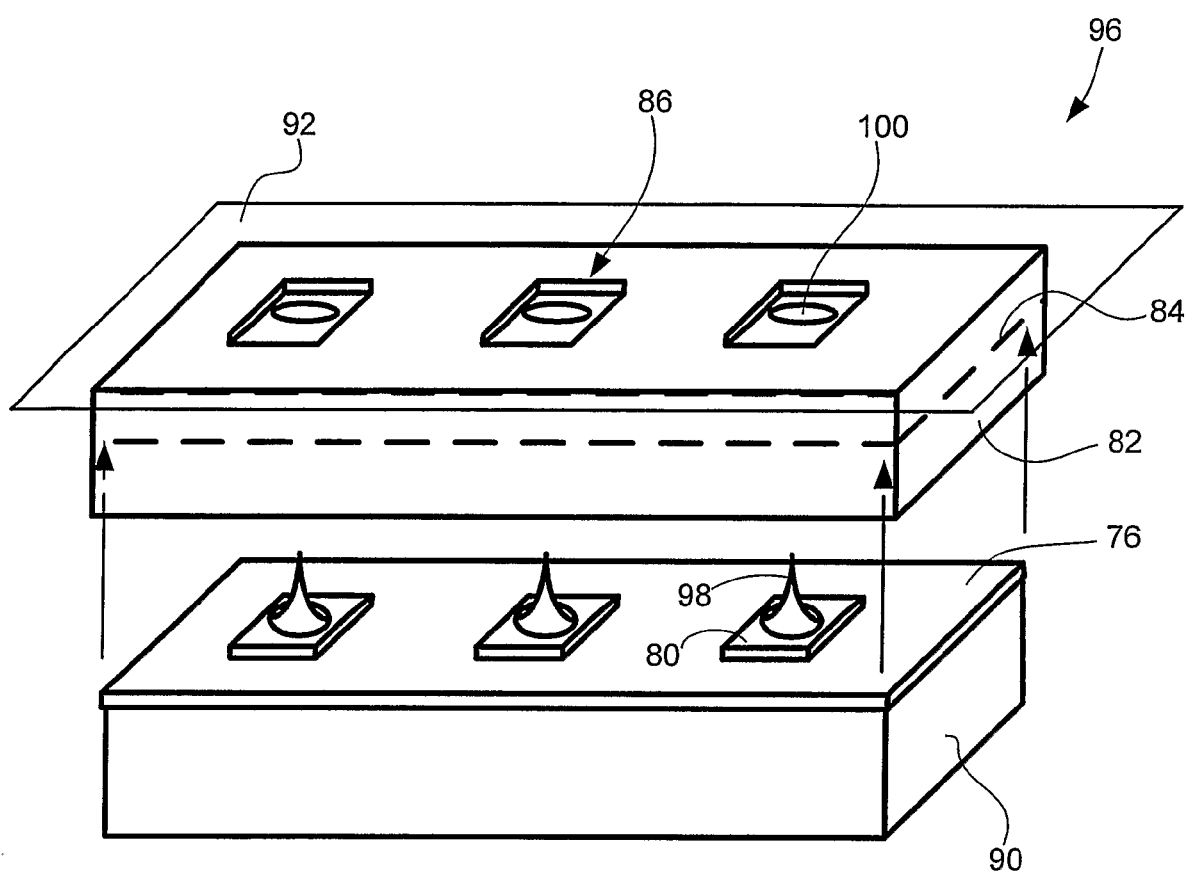
FIG. 11A schematically illustrates an exploded perspective view of an embodiment of an allergy testing system.
Figure 11B:
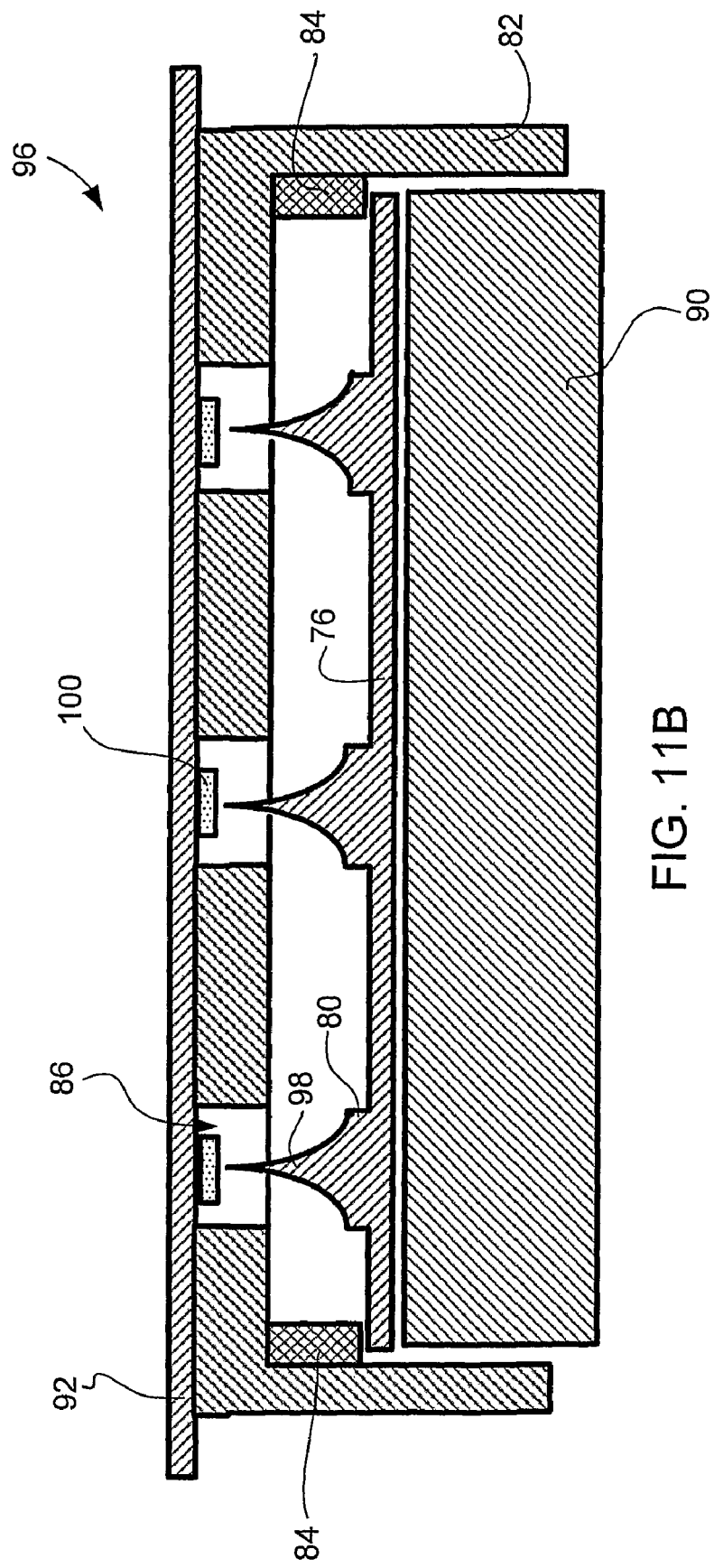
FIG. 11B schematically illustrates an assembled, cross-sectional view of the allergy testing system embodiment of FIG. 11A.

Referring to FIGS. 10A and 10B, another embodiment of a minimally invasive allergy testing system 74 is schematically illustrated in an exploded perspective view and an assembled side cross-sectional view, respectively. The allergy testing system includes a microneedle substrate 76 that supports an array of hollow microneedles 78 with integral mesas 80. The mesas 80 are not absolutely necessary, but in some embodiments, they can provide stability for the microneedles 78 as the microneedles are engaged. (This will be explained in more detail later.) A linear array of microneedles having mesas are illustrated in this embodiment, but other embodiments may have other numbers and types of components in other shapes and configurations. The substrate 76, microneedles 78, and mesas 80 may be manufactured from a number of different materials, such as silicon, glass, metal, or plastic. The microsystem allergy testing device 74 also includes a package assembly 82 which houses the substrate 76, microneedles 78, and mesas 80 such that the top surface of substrate 76 rests against a compressible stop 84 along an inner surface of the package 82. The compressible stop 84 may be permanently compressible, or may be an energy storage device such as a spring. The microneedles 78 are mounted for movement within the package 82 from a position where the upper tips of the microneedles 78 lie within orifices 86, such that they do not protrude significantly outside of the package assembly, to a position protruding outside of the package assembly 82.

An encapsulated set of allergens 88 associated with each hollow microneedle 78, is sandwiched between the substrate 76 and the plunger 90. The plunger 90 may be activated by an activation system (not shown), such as mechanical systems, electromechanical systems, piezoelectric, or a micromechanical actuator. Pressure applied to the plunger 90 causes the release of substrate 76 from resting stop 84 as well as the flow of allergens 88 through the channels associated with one of the hollow microneedles 78 positioned adjacent each encapsulated allergen. Motion of substrate 76 causes each of the microneedles 78 to protrude out of the package assembly 82 through the orifices 86 towards the patient's skin (not shown in this figure, but in this embodiment, the test subject would be above the allergy testing system 74 as oriented.) When the plunger is depressed far enough, the microneedles 78 pierce the patient's skin while mesas 80 fit into orifices 86 in package 82 to help increase travel and positional stability of the microneedles 78.

This embodiment also optionally has a thin sealing film 92 employed over a surface of the package assembly 82 to serve as a sterile layer between the subject's skin and the microneedles 78. Sealing film 92 may be removed before use or left behind on the patient's skin along with human readable, barcode, or other identifying marks 94. Such identifying marks have been discussed above with regard to previous embodiments.

Referring to FIGS. 11A and 11B, another embodiment of a minimally invasive allergy testing system 96 is schematically illustrated in an exploded perspective view and an assembled side cross-sectional view, respectively. The allergy testing device 96 illustrated in FIGS. 11A and 11B is similar in structure and operation to the allergy testing device 74 embodied in FIGS. 10A and 10B, except as described herein. In the embodiment of FIGS. 11A and 11B, solid microneedles 98 are used along with encapsulated allergens 100 that are located in the path between the microneedles 98 and the patient's skin (again, the skin is not illustrated in this embodiment, but the test subject would be above the allergy testing system 96 in the orientation illustrated.) As the plunger 90 is activated, microneedles 98 puncture the encapsulated allergens 100, releasing the allergens, and continue to move outward until they also penetrate the subject skin. After the patient's skin is pricked by the microneedles 98, the allergen is then free to penetrate.

FIGS. 12A-12C schematically illustrate one possible method of applying allergens to a subject using an embodiment of an allergy testing system. In a first step, FIG. 12A, the minimally invasive allergy testing system 102 is placed in contact with a subject's skin 36. Since this embodiment of an allergy testing system 102 has a sealing layer 92, that is the portion of the test system initially in contact with the skin 36. In other systems, the portion initially in contact with the skin 36 might be the package assembly 82. In FIG. 12A, the microneedle array is in a resting position. In a second step, FIG. 12B, the plunger 90 is activated, in the orientation of FIG. 12B, in a downward direction, causing the substrate 76 to compress the compressible stop 84. This causes the microneedles 98 to puncture the encapsulated allergens 100, the sealing layer 92, and then the skin 36. In FIG. 12B, the microneedle array 98 is in an penetrating position. If the compressible stop 84 is an energy storage device, such as a memory foam or a spring, then in a further step, FIG. 12C, the compressible stop 84 retracts the substrate 76 and therefore lifts the microneedles 98 from the skin 36 and substantially back into the resting position. The encapsulated allergens 100 are allowed to enter the puncture holes in the optional sealing layer 92 and the holes in the skin 36. The various possible needle shapes and geometries have been discussed earlier, and the microneedle shapes illustrated in this example are not intended to be limiting. Furthermore, microneedles of differing lengths on the same substrate 76 may be used. A benefit of providing different length microneedles may be to allow different allergens to reach a targeted skin depth, or to test the same allergen at different depths for studied comparisons.

Figures 3, 12D:
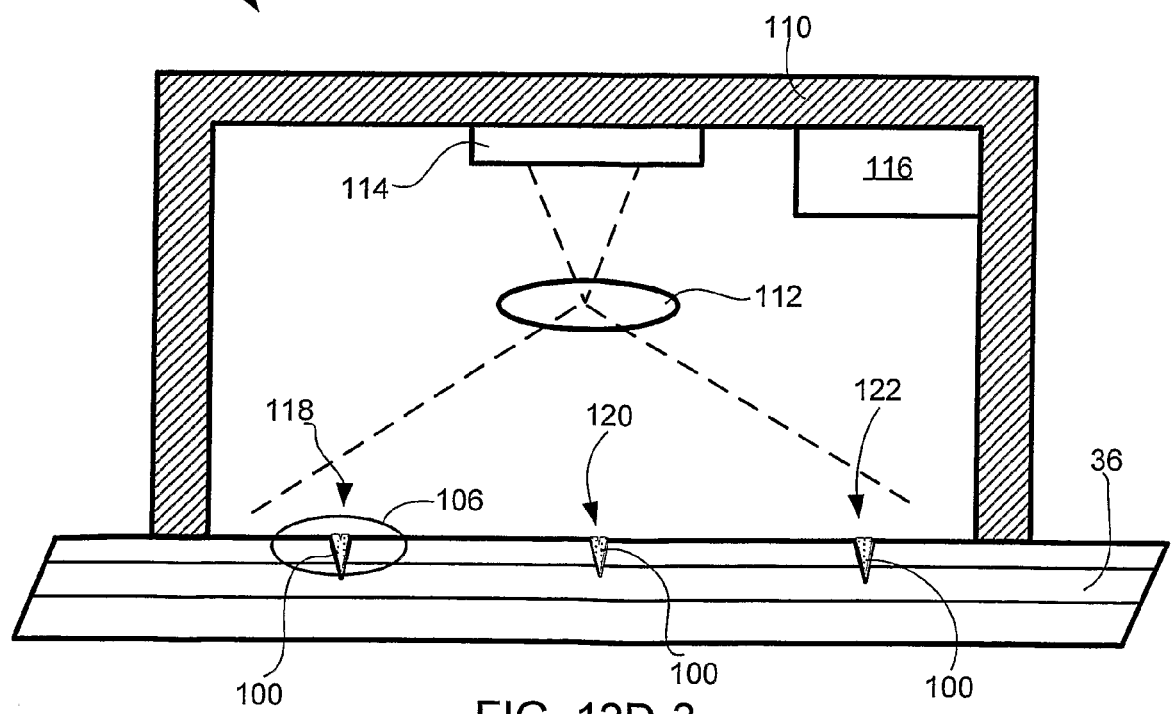
Figures 4, 12D:
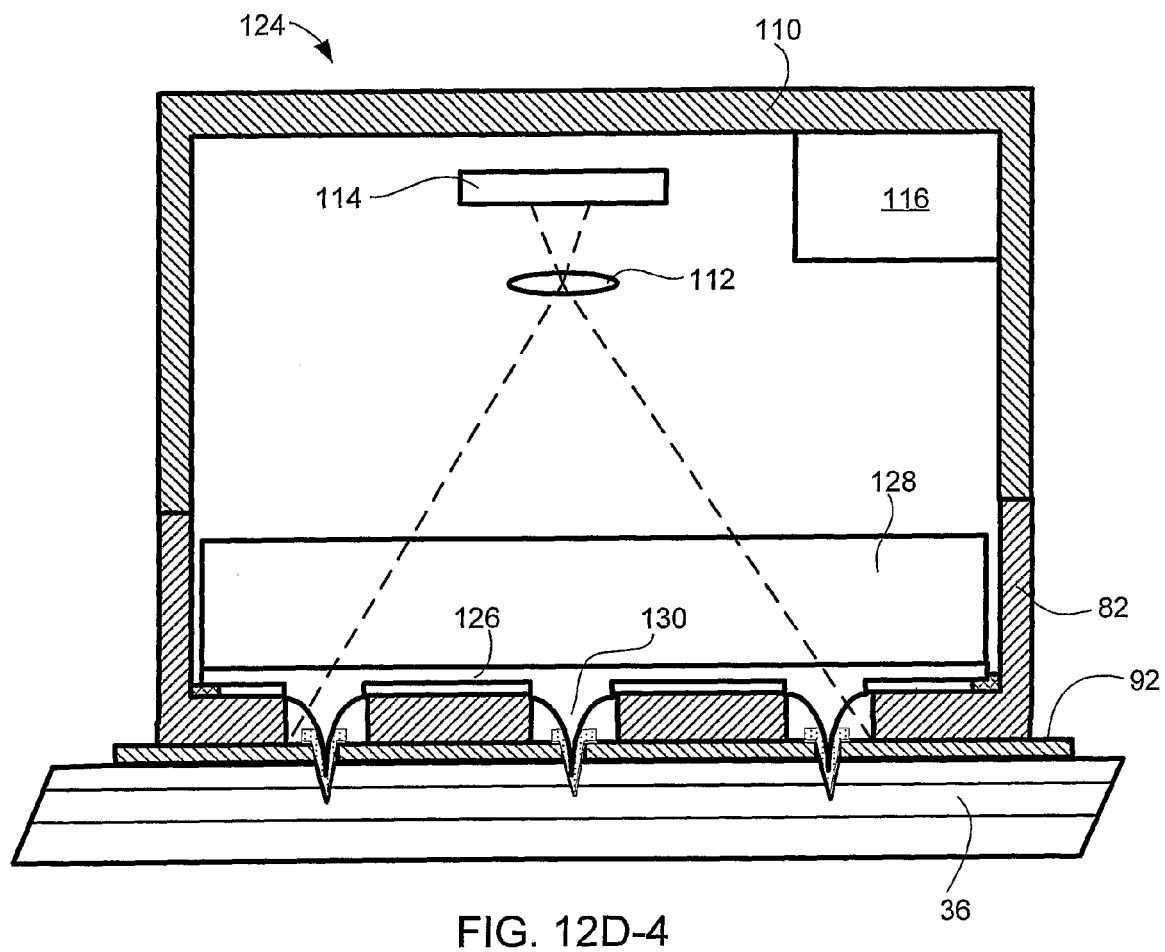

FIGS. 12D1-12D4 schematically illustrate different embodiments of gathering and analyzing allergy test data after the allergens have been applied by the allergy testing system in FIGS. 12A-12C. FIG. 12D1 schematically illustrates a test subject's skin 36 which has been pricked and injected with allergens 100 by the microneedles 98 of a minimally invasive allergy testing system 102. In the embodiment of FIG. 12D1, the sealing layer 92 has been removed, prior to manual viewing of the test results. Here, a schematic human eye 104 is looking for a reaction 106 to a particular allergen. While the allergy test results may be evaluated using a manual approach such as this, other methods may make it easier to distinguish results given the close spacings between allergy test points possible with microneedles. If the sealing layer 92 is left in place, as in FIG. 12D2, patient information, test identification, and allergen identification may be aided by markings on the sealing layer as left behind on the skin 36.

FIG. 12D3 schematically illustrates an embodiment of an allergy analysis system 108 which can optionally be used in place of or in conjunction with manual evaluation methods. The allergy analysis system 108 includes a module 110 with imaging optics 112. The imaging optics 112 focuses images of the tested skin area on an image sensor 114. The image sensor 114 is coupled to an image analyzer or processor 116. The image analyzer 116 can analyze the captured images for color, shape, dimension, and location in the test field. Based on this analysis and correlation with what allergen was tested in which location, the analyzer 116 determines reactivity data for each allergen. The reactivity data, as well as the captured images may be stored, displayed, transmitted, and/or printed by the analyzer 116. Optionally, the analyzer may output this data to another processor for storage, display, further analysis, transmission, and/or printing. In the embodiment of FIG. 12D3, the analyzer 116 is directly coupled to the allergy analysis system 108. In other embodiments, the analyzer 116 may be remotely coupled to the analysis system 108 via a wireless or cabled link.

The image analyzer 116 may comprise a central processing unit (CPU) or processor and a memory which are coupled together by a bus or other link, although other numbers and types of components in other configurations and other types of systems, such as an application specific integrated circuit (ASIC) could be used. The processor may execute a program of stored instructions for one or more aspects of the claimed invention, including the method for determining a degree of reaction to one or more allergens as described and illustrated herein. The memory stores these programmed instructions for execution by the processor. A variety of different types of memory storage devices, such as random access memory (RAM) or a read only memory (ROM) in the system or a floppy disk, hard disk, CD ROM, or other computer readable medium which is read from and/or written to by a magnetic, optical, or other reading and/or writing system that is coupled to the processor, can be used for the memory to store these programmed instructions.

In the example of FIG. 12D3, the skin puncture site 118 shows a positive allergy reaction 106, while skin puncture sites 120, 122 show negative allergy reactions. The imaging module 110 should be placed in alignment with the original allergy testing device 102 (from FIGS. 12A-12C) such that the imaging optics 112 creates images of test sites 118, 120, and 122. These test sites 118, 120, 122 are associated with each allergen in correlated locations on image sensor 114. Image patterns associated with each allergen, as imaged by sensor 114, are captured and transmitted to image analyzer 116 for analysis as described above in order to identify color, shape, dimension, allergic reaction, and/or a time rate of change of the allergic response. The determination of a time rate of change in the allergic response may be a great benefit to medical professionals who often do not have the time to manually observe a reaction on a continuous or substantially continuous basis that would let them see how allergic reactions vary over time.

In other embodiments of an allergy testing system which have an allergy imaging analysis system 108, it may be important to determine topographic information when assessing reactivity to an allergen. In such embodiments, an extra set of imaging optics and an extra image sensor may be displaced laterally from the other optical system to obtain stereoscopic, parallax information about a given test location. Parallax information may in turn be used to calculate topographic profiles of test regions.

FIG. 12D4 schematically illustrates an embodiment of a minimally invasive allergy testing system 124 with an integrated imaging and analysis module 110. The microneedle array 126 and plunger 128 operate in similar fashion to the corresponding elements in FIG. 12A, except as described herein. In this embodiment, the array of microneedles 126 and plunger 128 are made of glass or some other transparent material, such as transparent hard plastic, such that imaging module 110 may image the tested regions with the needles in-situ, or even slightly or completely retracted. Preferably, the width of the microneedles 130 relative to their spacing should be fine enough to allow enough imaging area for an adequate diagnosis of the allergic reaction.

Figure 13:
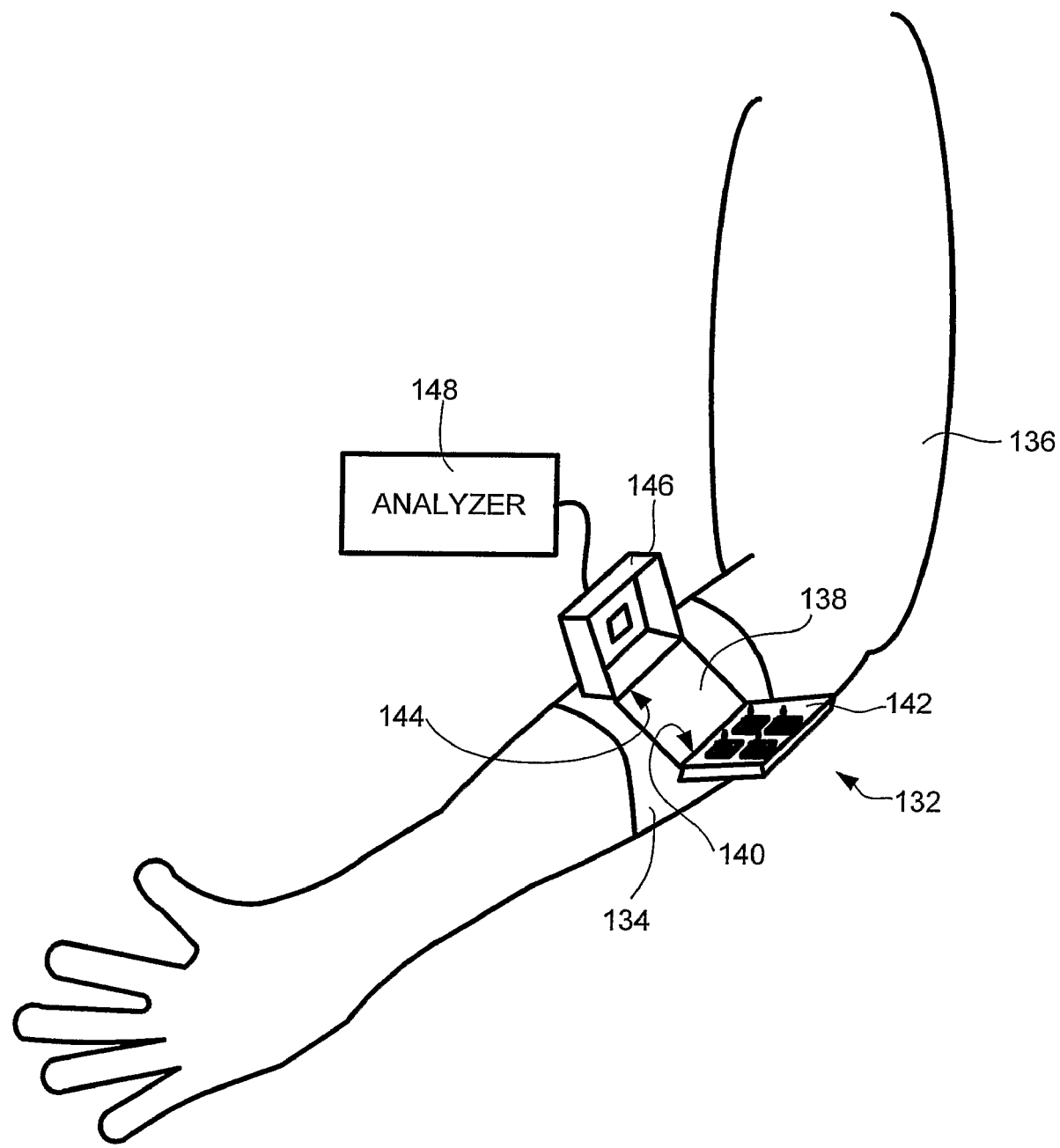
FIG. 13 schematically illustrates an embodiment of an allergy testing system.

FIG. 13 schematically illustrates a further embodiment of a minimally invasive allergy testing system 132. The allergy testing system 132 is coupled to a band 134 which may be wrapped around a portion of a person's body. In this example, the part of the body illustrated is an arm 136. Of course, it would be apparent to those skilled in the art that attachment band 134 could be compatible with or modified to attach to other portions of the body. Attachment band 134 need not circle completely around and back to itself, although preferred embodiments may have Velcro® attachments which wrap around the body and then connect to themselves. The purpose of the attachment band 134 is to hold a test frame 138 in substantially the same position during a minimally invasive allergy test. The test frame 138 defines an opening in the band 134 through which the skin may be accessed. The test frame 138 also has a first alignment coupling, such as a hinge 140 onto which a package 142 containing a microneedle array and encapsulated allergens may be placed for aligned engagement with the skin in the test frame 138. The test frame 138 has a second alignment coupling, such as a hinge 144 onto which an allergy imaging system 146 may be placed for aligned engagement with the skin in the test frame 138. In some embodiments, the allergen and microneedle package 142 will be engaged with the test frame at different times from the imaging system 146. In other embodiments, such as the transparent embodiments, both the allergen and microneedle package 142 and the imaging system 146 may be engaged at the same time. In various embodiments, the alignment coupling does not have to be a hinged connection. It may, instead, be a temporary guide for the manual placement of an otherwise loose portion of the testing system, such as the allergen package, or the imaging system. In the embodiment of FIG. 13, the analyzer 148 is illustrated as being remotely coupled to the imaging system 146. This remote link may be a physical wire or a radio frequency (RF) or optical wireless link.

Figure 14A:
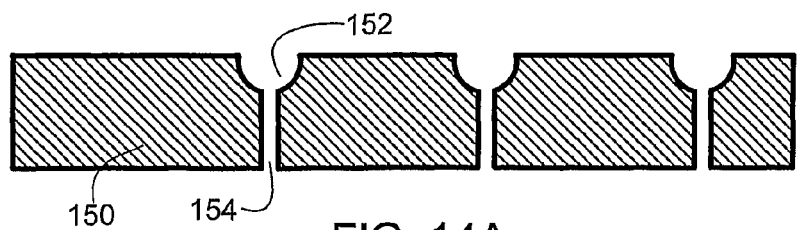
FIGS. 14A-14P schematically illustrate an embodiment of a process for manufacturing a replaceable allergen cartridge for use in an allergy testing system.
Figure 14B:
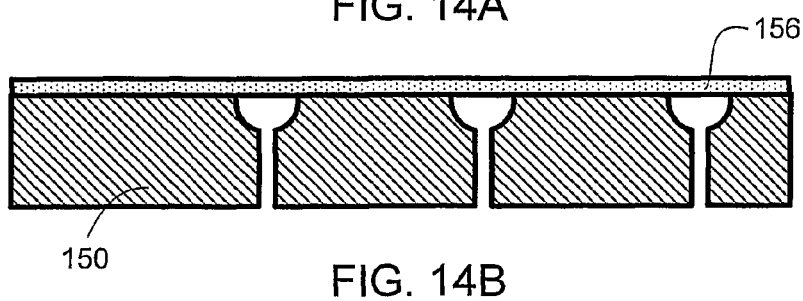
Figure 14C:
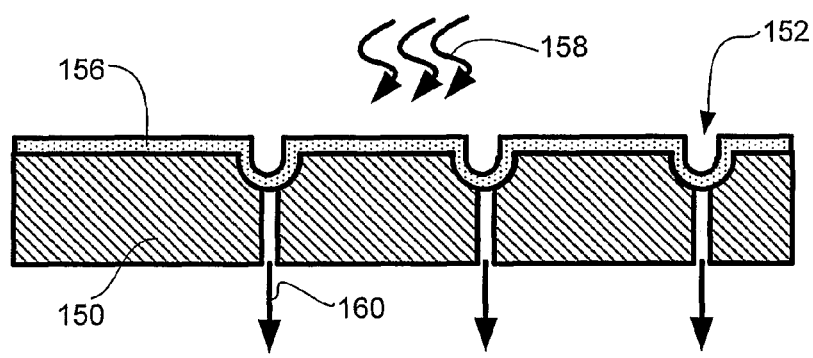
Figure 14D:
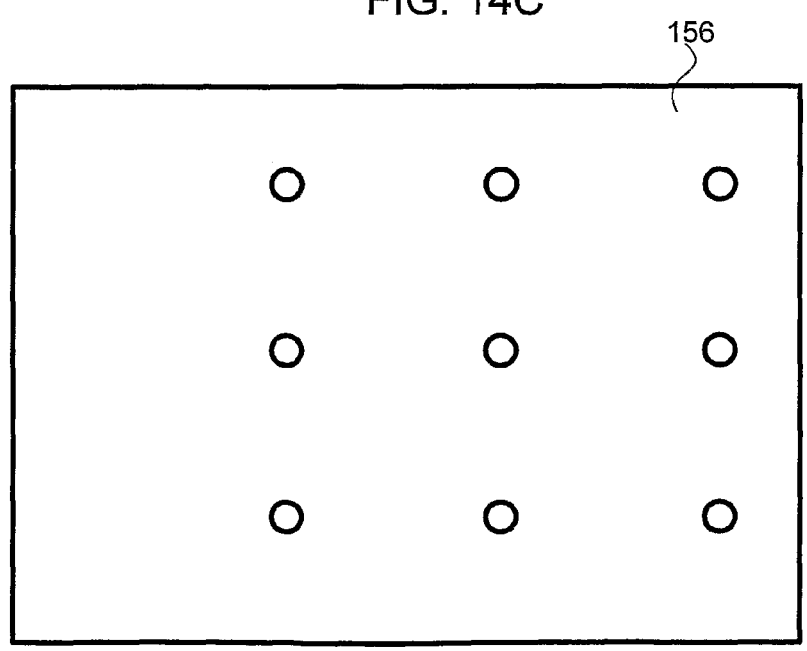

All of the minimally invasive allergy testing systems embodied herein, and their equivalents, are intended to be used with replaceable cartridges having the microneedle array and the encapsulated allergens. FIGS. 14A-14P schematically illustrate an embodiment of a process for manufacturing a replaceable allergen cartridge for use in an allergy testing system.

The process begins, FIG. 14A, with a mold 150, having cavities 152 and vacuum lines 154 coupled to each cavity. Next, FIG. 14B, a formable layer 156 is placed on top of the mold 150. An example of a material which may be used for the formable layer 156 is polyvinylidene chloride (PVDC). Next, FIG. 14C, heat 158 is applied to the PVDC 156, while a negative pressure 160 is applied to the vacuum lines 154 from the back side of the mold 150. This causes the PVDC 156 to fill the mold cavities 152. A top view of the PVDC 156 coating the mold 150 may be seen in FIG. 14D.

Figure 14E:
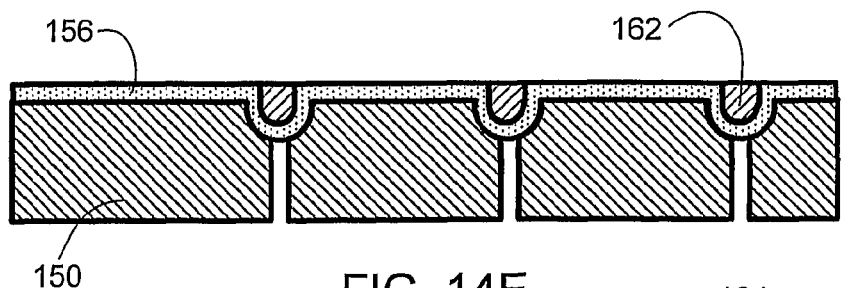
Figure 14F:
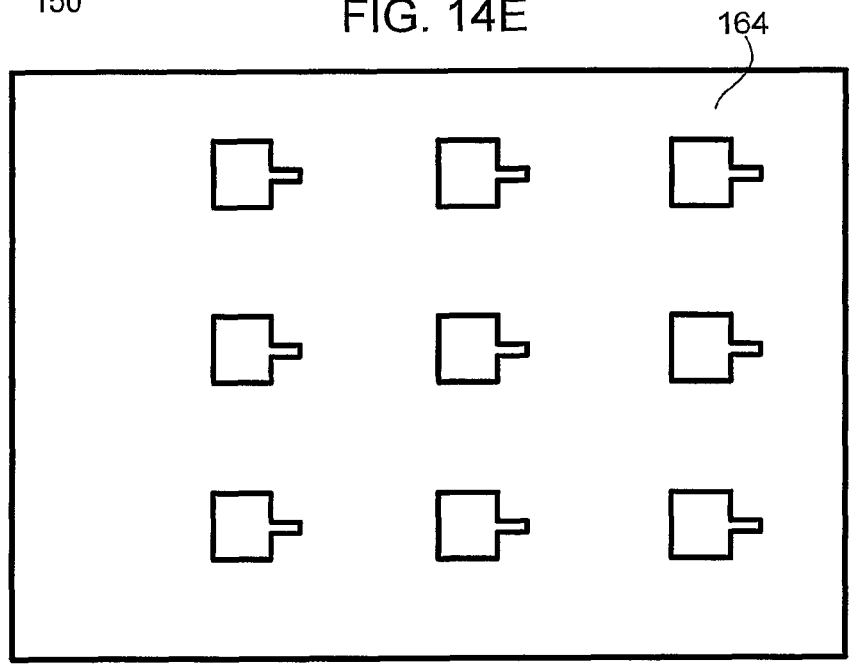
Figure 14G:
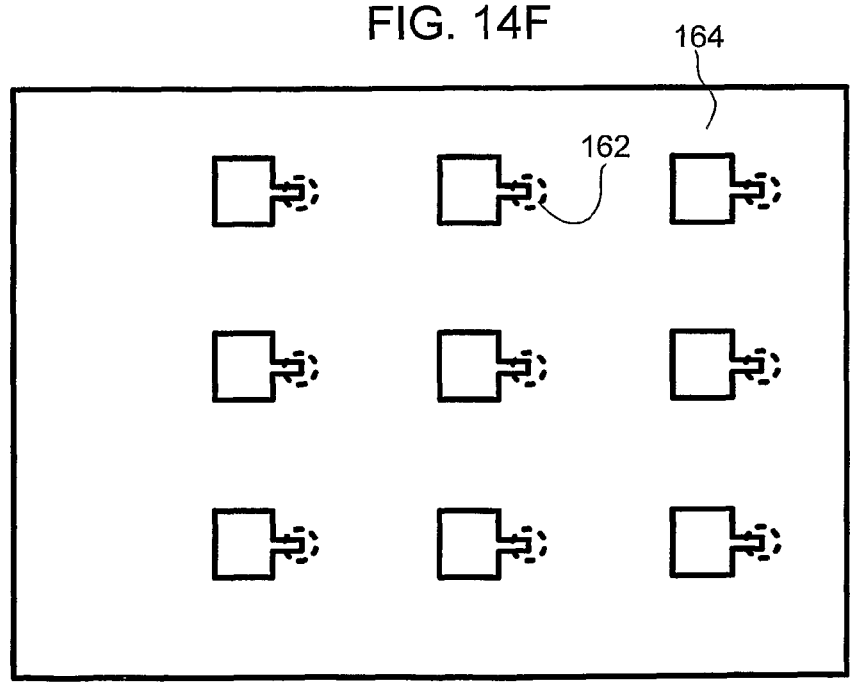
Figure 14H:
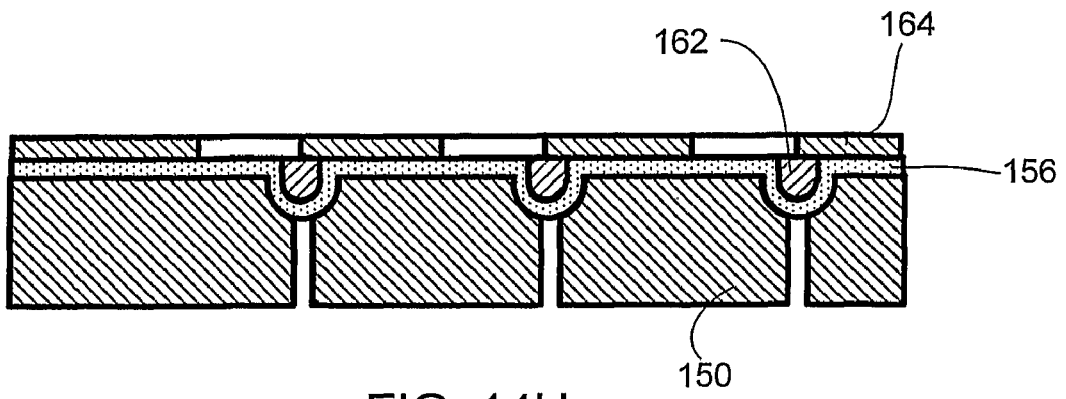
Figure 14J:
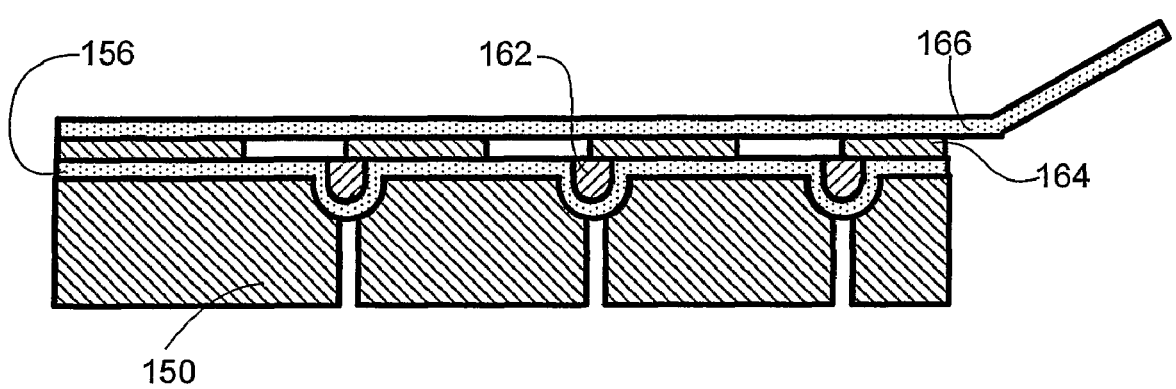
Figure 14K:
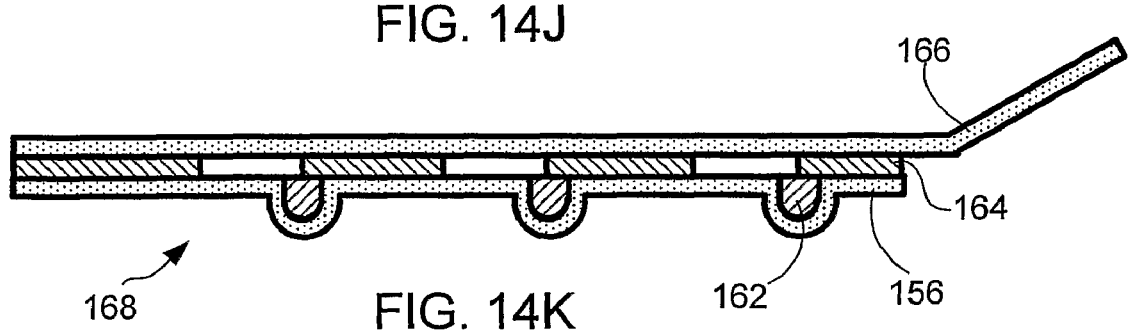

Next, FIG. 14E, allergens 162 are filled into the PVDC-wrapped cavities. The array of allergens do not have to be the same, but may be any combination of unique allergens and/or repeats. A plastic cover 164, such as the one shown in a top view in FIG. 14F may then be applied, FIG. 14G, to the top of the array of allergens 162. FIG. 14H illustrates the assembly package of FIG. 14G in a side view. Next, FIG. 14J, a removable seal 166 is applied to the top of the package. The mold 150 can then be removed, leaving the encapsulated allergens 168 as illustrated in FIG. 14K.

Figure 14L:
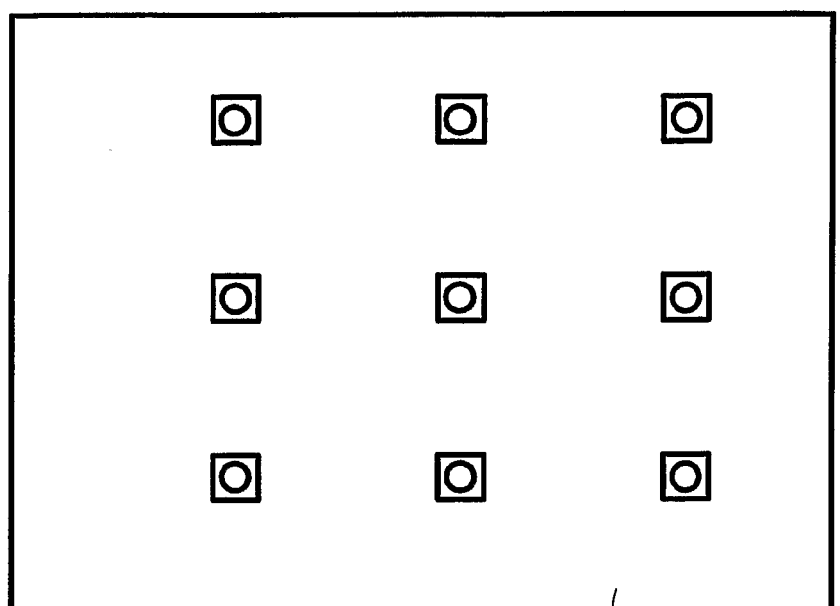
Figure 14M:
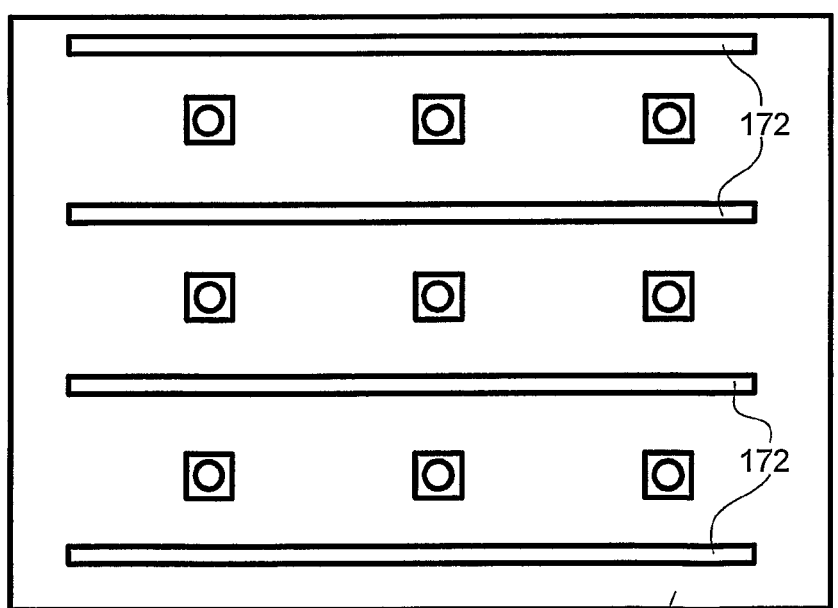
Figure 14N:
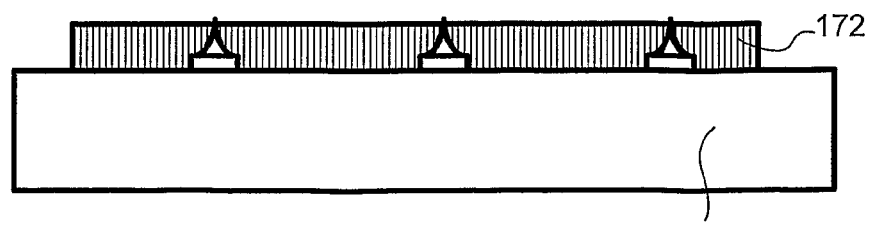
Figure 14P:
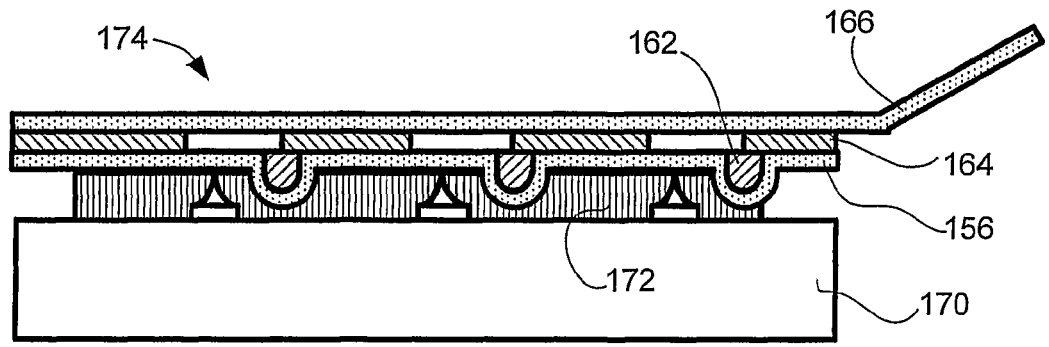

In a parallel, preceding, or subsequent step, FIG. 14L, a microneedle array 170 is formed out of silicone, glass, plastic, quartz, or metal. Suitable methods of microneedle construction have been discussed above. Next, FIG. 14M, elastomer springs 172 are coupled to the substrate of the microneedle array 170. FIGS. 14L and 14M show the microneedle array 170 in a top view. FIG. 14N shows the microneedle array 170 and the elastomer springs 172 in a side view. The elastomer springs in this embodiment are just one type of energy storage device which may be coupled to the microneedle array 170. Other embodiments may have energy storage devices which include metal springs and plastic springs.

Next, the allergen array assembly 168 from FIG. 14K and the microneedle array assembly from FIG. 14N are coupled together as in FIG. 14P to form a replaceable allergen cartridge 174. The coupling of the two sections may be accomplished with adhesives, shrink wrapping, or packaging.

Figure 15A:
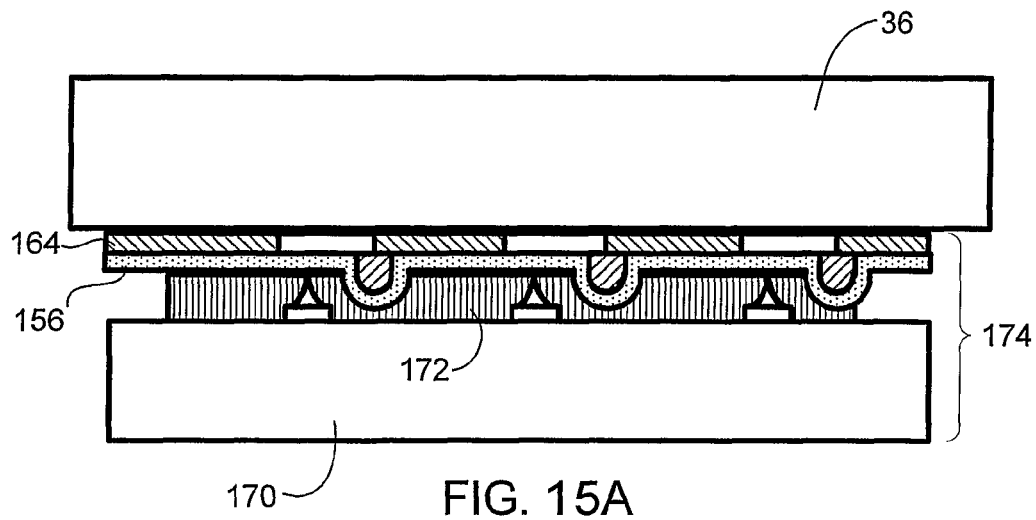
FIGS. 15A and 15B schematically illustrate an embodiment of a process for allergy testing using the replaceable allergen cartridge of FIG. 14P.
Figure 15B:
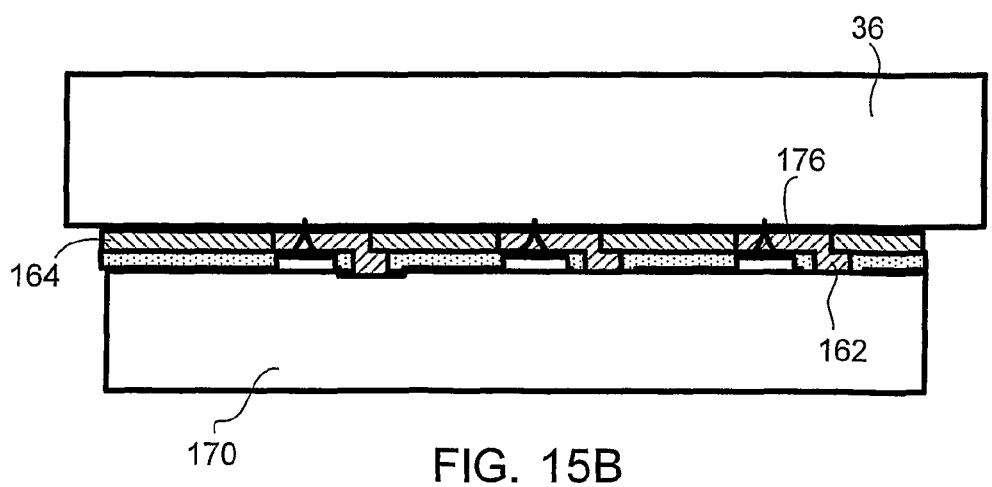

FIGS. 15A and 15B schematically illustrate an embodiment of a process for allergy testing using the replaceable allergen cartridge 174 of FIG. 14P. FIG. 15A illustrates the replaceable cartridge 174 in contact with skin 36 after peeling away the removeable seal 166. Previous discussions have covered the activation systems and imaging systems which may be used with the microneedle array and encapsulated allergen components of the replaceable cartridge. For simplicity, and to avoid duplication, those other elements are not shown here. Instead, FIG. 15B illustrates how the encapsulated allergens in this embodiment of a replaceable allergen cartridge may be compressed into the puncture area 176 of the microneedles.

Although the descriptions and figures of the embodiments described above show single needle arrays or one dimensional array systems, the claimed invention is easily extendible to two dimensions.

Having thus described several embodiments of the claimed invention, it will be rather apparent to those skilled in the art that the foregoing detailed disclosure is intended to be presented by way of example only, and is not limiting. Various alterations, improvements, and modifications will occur and are intended to those skilled in the art, though not expressly stated herein. These alterations, improvements, and modifications are intended to be suggested hereby, and are within the spirit and the scope of the claimed invention. Additionally, the recited order of the processing elements or sequences, or the use of numbers, letters, or other designations therefore, is not intended to limit the claimed processes to any order except as may be specified in the claims. Accordingly, the claimed invention is limited only by the following claims and equivalents thereto.

What is claimed is:
1. An allergy testing system, comprising:
encapsulated allergens;
a microneedle array;
an activation system coupled to the microneedle array and the encapsulated allergens such that the encapsulated allergens are moved into contact with a subject as the microneedle array is moved from a resting position to a penetrating position;
at least one imaging system configured to capture a plurality of images of penetration sites by the microneedle array;
at least one image sensor;
an imaging optics system which focuses the images of penetration sites on the at least one image sensor;
a second image sensor;
a second imaging optics system which focuses the images of the penetration sites on the second image sensor, wherein the image sensors are used to determine a topographic profile of an allergic reaction; and
an analyzer coupled to the at least one imaging system and configured to analyze the plurality of images to determine a time rate of change of an allergy response to one or more of the allergens.

2. The allergy testing system of claim 1, wherein the microneedle array pierces the encapsulated allergens while moving to the penetrating position.

3. The allergy testing system of claim 1, wherein the encapsulated allergens are coupled between the activation system and the microneedle array, and the encapsulated allergens are released by a pressure exerted on the encapsulated allergens by the activation system as the microneedle array is moved to the penetrating position.

4. The allergy testing system of claim 1, wherein at least one microneedle in the microneedle array comprises a hollow needle.

5. The allergy testing system of claim 1, wherein at least one microneedle in the microneedle array comprises a grooved needle.

6. The allergy testing system of claim 1, wherein at least one microneedle in the microneedle array comprises a corrugated needle.

7. The allergy testing system of claim 1, wherein the microneedle array comprises at least one needle of a first penetration depth and at least one needle of a second penetration depth which is different from the first penetration depth.

8. The allergy testing system of claim 1, wherein the microneedle array comprises at least one needle with a cross-section that is selected from the group consisting of: square, rectangular, triangular, and circular.

9. The allergy testing system of claim 1, wherein the microneedle array comprises at least one needle with a varying cross-section.

10. The allergy testing system of claim 1, wherein the microneedle array comprises silicon.

11. The allergy testing system of claim 1, wherein the microneedle array comprises glass.

12. The allergy testing system of claim 1, wherein the microneedle array comprises quartz.

13. The allergy testing system of claim 1, wherein the microneedle array comprises a substantially transparent material.

14. The allergy testing system of claim 1, further comprising a package that at least partially encloses the microneedle array and the encapsulated allergens, wherein the microneedle array is moveable within orifices in the package.

15. The allergy testing system of claim 14, further comprising at least one sheet covering the orifices to enclose at least one portion of the microneedle array.

16. The allergy testing system of claim 1, wherein the plurality of images of penetration sites captured by the imaging system comprise continuous images of the penetration sites.

17. The allergy testing system of claim 1, wherein the activation system comprises a mechanical system.

18. The allergy testing system of claim 1, wherein the activation system comprises an electromechanical system.

19. The allergy testing system of claim 1, wherein the activation system comprises a piezoelectric system.

20. The allergy testing system of claim 1, wherein the activation system comprises a micromechanical actuator.

21. The allergy testing system of claim 1, wherein the activation system is configured to be manually actuated.

22. An allergy testing system, comprising:

encapsulated allergens;

a microneedle array;

an activation system coupled to the microneedle array and the encapsulated allergens such that the encapsulated allergens are moved into contact with a subject as the microneedle array is moved from a resting position to a penetrating position;

at least one imaging system configured to capture a plurality of images of penetration sites by the microneedle array;

an analyzer coupled to the at least one imaging system and configured to analyze the plurality of images to determine a time rate of change of an allergy response to one or more of the allergens; and an alignment guide configured to be captured in the plurality of images captured by the at least one imaging system of the penetration sites by the microneedle array;

wherein the analyzer is further configured to utilize the alignment guide in the captured plurality of images for an orientation of the plurality of images as part of the analysis of the plurality of images.

23. The allergy testing system of claim 22, wherein the alignment guide is a barcode near the allergy test area.

24. The allergy testing system of claim 22, wherein the alignment guide comprises a computer recognizable pattern of needle pricks in an image captured by the at least one imaging system of the allergy test area.

25. An allergy testing system, comprising:

encapsulated allergens;

a microneedle array;

an activation system coupled to the microneedle array and the encapsulated allergens such that the encapsulated allergens are moved into contact with a subject as the microneedle array is moved from a resting position to a penetrating position;

at least one imaging system configured to capture a plurality of images of penetration sites by the microneedle array;

an analyzer coupled to the at least one imaging system and configured to analyze the plurality of images to determine a time rate of change of an allergy response to one or more of the allergens;

an attachment band having a test frame, wherein the test frame defines an opening in the attachment band; and a package, for interfacing with the test frame, the package comprising the microneedle array and the encapsulated allergens;

wherein the imaging system is configured to interface with the test frame.

26. The allergy testing system of claim 25, further comprising: a first alignment coupling for removeably coupling the package to the test frame; and a second alignment coupling for removeably coupling the imaging system to the test frame.

27. The allergy testing system of claim 26, wherein the package and the imaging system can be coupled to the test frame at the same time.

28. The allergy testing system of claim 1, wherein the imaging system is further configured to capture the one or more images of penetration sites after the microneedle array is moved away from the penetrating position.

29. The allergy testing system of claim 1, wherein the imaging system is further configured to wait for a first period of time after moving to the penetrating position before the capturing of the one or more images.

30. The allergy testing system of claim 1, wherein the allergy testing system is further configured to output reactivity data comprising a topographic indicator of an allergic reaction.

31. An allergy testing system, comprising:

a) encapsulated allergens;

b) a microneedle array;

c) an activation system coupled to the microneedle array and the encapsulated allergens such that the encapsulated allergens are moved into contact with a subject as the microneedle array is moved from the resting position to a penetrating position;

d) a package that at least partially encloses the microneedle array and the encapsulated allergens, wherein the microneedle array is moveable by the activation system within orifices in the package;

e) at least one sheet covering the orifices to enclose at least one portion of the microneedle array;

f) at least one imaging system that captures one or more images of penetration sites by the microneedle array, wherein the imaging system comprises:

1) at least one image sensor; and 2) an imaging optics system which focuses the images of penetration sites on the at least one image sensor;

g) an attachment band having a test frame, wherein the test frame defines an opening in the attachment band;

h) a first alignment coupling for removeably coupling the package to the test frame;

i) a second alignment coupling for removeably coupling the at least one imaging system to the test frame; and j) an analyzer coupled to the imaging system.

* * * * *